United States Patent [19]
Tesk et al.

[11] 4,053,308

[45] * Oct. 11, 1977

[54] NONPRECIOUS ALLOY FOR FUSION TO PORCELAIN

[75] Inventors: John A. Tesk, Woodridge; Ronald P. Dudek, River Grove; Peter Kosmos, Alsip, all of Ill.

[73] Assignee: Howmedica, Inc., New York, N.Y.

[ * ] Notice: The portion of the term of this patent subsequent to Sept. 23, 1992, has been disclaimed.

[21] Appl. No.: 536,328

[22] Filed: Dec. 24, 1974

[51] Int. Cl.[2] .............................................. C22C 19/05

[52] U.S. Cl. .......................................... 75/171; 148/32

[58] Field of Search .................... 75/171, 170; 148/32, 148/32.5

[56] References Cited

U.S. PATENT DOCUMENTS 2,460,590 2/1949 Lohr ........................................ 75/171
3,005,704 10/1961 Faulkner ................................. 75/171

*Primary Examiner*—R. Dean
*Attorney, Agent, or Firm*—Connolly and Hutz

[57] ABSTRACT

A nonprecious alloy for dental restorations fused to porcelain includes the following ranges of constituents in percentages by weight:

| Constituent | Proportional Range |
|---|---|
| Nickel | Balance |
| Chromium | 10.0–22.0 |
| Aluminum | 1.0–5.0 |
| Silicon | 0.5–2.0 |
| Manganese | 0.01–0.2 |
| Molybdenum | 0.0–7.0 |
| and one of the following Groups A or B: | |
| Group A | |
| Strontium, lanthanum and/or zirconium individually or as a combination of strontium and zirconium, and | 0.2–2.0 |
| either iron or tungsten separately or in combination | 0.0–5.0 |
| Group B | |
| Strontium, lanthanum and/or zirconium individually or as a combination of strontium and zirconium, | 0.0–2.0 |
| gallium, and | 1.0–3.0 |
| iron | 0.0–1.0 |

10 Claims, No Drawings

NONPRECIOUS ALLOY FOR FUSION TO PORCELAIN

A metal alloy for making a dental restoration must be strong, tough, resistant to tarnish, oxidation and corrosion, compatible with the human oral environment, (biocompatible), have a suitable coefficient of thermal expansion, be fusible to porcelain and have good castability. Most effective dental alloys are relatively expensive because of their high noble metal content. An object of this invention is to provide a highly effective and relatively simple and economical nonprecious alloy suitable for dental use including fusibility to porcelain.

In accordance with this invention a highly effective and relatively economical nonprecious alloy for dental use incorporates the following ranges of constitutents in percentages by weight.

| Constituent | Proportional Range |
|---|---|
| Nickel | Balance |
| Chromium | 10.0–22.0 |
| Aluminum | 1.0–5.0 |
| Silicon | 0.5–2.0 |
| Manganese | 0.01–0.2 |
| Molybdenum | 0.0–7.0 |
| and one of the following Groups A or B: | |
| Group A | |
| Strontium, lanthanum and/or zirconium individually or as a combination of strontium and zirconium, and | 0.2–2.0 |
| either iron or tungsten separately or in combination | 0.0–5.0 |
| Group B | |
| Strontium, lanthanum and/or zirconium individually or as a combination of strontium and zirconium, | 0.0–2.0 |
| gallium, and | 1.0–3.0 |
| iron | 0.0–1.0 |

Particular examples of alloys of this invention are listed below in Examples I–III giving preferred compositions and proportional ranges in percentages by weight. These alloys have been found particularly useful for dental service and are particularly effective for fusion and tight adherance to porcelain.

EXAMPLE I

| Element | Preferred Composition | Composition Range |
|---|---|---|
| Nickel | 75.4 | Balance |
| Chromium | 13.5 | 10.0–15.0 |
| Molybdenum | 5.0 | 1.0–7.0 |
| Aluminum | 3.0 | 1.0–5.0 |
| Silicon | 1.0 | 0.5–2.0 |
| Manganese | 0.1 | 0.01–0.2 |
| Iron | 1.5 | 0–5.0 |
| Strontium, Lanthanum and/or Zirconium individually or as a combination of Strontium and Zirconium | 0.5 | 0.2–2.0 |
| | 100.0% | |

EXAMPLE II

| Element | Preferred Composition | Composition Range |
|---|---|---|
| Nickel | 78.4 | Balance |
| Chromium | 13.5 | 10.0–15.0 |
| Molybdenum | 1.5 | 1.0–5.0 |
| Aluminum | 3.0 | 1.0–5.0 |
| Silicon | 1.0 | 0.5–2.0 |
| Manganese | 0.1 | 0.01–0.2 |
| Strontium, Lanthanum and/or Zirconium individually or as a combination of Strontium and Zirconium | 0.5 | 0.2–2.0 |
| Tungsten | 2.0 | 0.5–5.0 |
| | 100.0% | |

-continued

EXAMPLE III

| Element | Preferred Composition | Composition Range |
|---|---|---|
| Nickel | 78.1 | Balance |
| Chromium | 13.5 | 10.0–22.0 |
| Molybdenum | 1.5 | 0.0–3.0 |
| Aluminum | 3.0 | 1.0–5.0 |
| Silicon | 1.0 | 0.5–2.0 |
| Manganese | 0.1 | 0.01–0.2 |
| Strontium, Lanthanum and/or Zirconium individually or as a combination of Strontium and Zirconium | 0.5 | 0.0–2.0 |
| Gallium | 2.0 | 1.0–3.0 |
| Iron | 0.3 | 0.0–1.0 |
| | 100.0% | |

All combinations of strontium, lanthanum and zirconium within the recited ranges are effective and a useful such constituent is a 50—50% combination of strontium and zirconium.

The bonding system that is necessary to achieve optimum bonding between the alloy and the porcelain is as follows:

| Constituent | Proportions |
|---|---|
| Gold Powder (5–15 microns) | 34.96 |
| Hi-Life Body Porcelain | 26.22 |
| Zirconium oxide (10 microns) | 8.74 |
| Bonding Agent Liquid | 30.08 |

Hi-Life is a trademark of Howmedica Inc., Dental Division, Chicago, Ill. for a porcelain having approximately the following forumlation in percentages by weight.

| Constituent | Composition |
|---|---|
| $SiO_2$ | 68.64 |
| $Al_2O_3$ | 13.76 |
| CaO | 0.36 |
| $K_2O$ | 13.46 |
| $Na_2O$ | 2.29 |
| $Li_2O$ | 1.49 |

The porcelain can also be any porcelain which has a similar formulation, is intended for fabrication of fused porcelain prostheses, and has a softening point of about 1200°–1400° F.

The bonding agent liquid is a low fusing "flux" soluble in a vehicle such as glycerine or an alcohol. The flux may be boron oxide or its salts, such as sodium borate or light element oxides, i.e. $Li_2O$, $Na_2O$ and those light element oxides of the first column of the periodic table. The essential characteristic is that the flux will react with the porcelain and with oxides which are formed on the alloy during firing of the bonding agent, to produce a low solubility, high tenacity, adherent intermediate layer of oxides to which porcelain will adhere during subsequent application and firing. A range of compositions can be effective under these conditions — a typical range would be that involving the following composition:

500 cc. glycerine

10—30 grams boric anhydride 1.14 cc. wetting agent

Another highly suitable bonding agent utilizing the addition of a thixotropic agent such as Cab-o-Sil, maintains all powders in solution for more consistent application and improve the "painting" characteristics.

Such a formulation is as follows by weight percent

| | |
|---|---|
| Glycerine | 94.954 |
| $B_2O_3$ | 2.502 |
| Victawet No. 12 | 0.237 |
| Cab-o-sil | 2.307 |

Victawet #12 is the trademark of Victor Chemical Works for a non-foaming, non-ionic wetting agent of the type $(RO)PO(OR')_2$, where R is a medium-chain alkyl group, and R' is a water-solubilizing group. $P_2O_5$ content is 16%. It is an amber-colored liquid; sp.gr. 1.121; pH, 4.7 (0.5% solution); surface tension, 28.8 dynes/cm. (0.2% solution 29° C); Draves test, 9.2 sec. at 0.6% conc., and 32 sec. at 0.2% conc. (in hard water) insoluble in naphtha; soluble in alcohols, acetone toluene; forms a milky solution in water. Uses: As a wetting agent in acid and alkaline solutions; and as a carrier for acid dyes. It provides level shades and uniform penetration in package dying of nylon, etc.

Cab-o-sil is the trademark of Godfrey L. Cabot, Inc. for a colloidal silica prepared in a hot gaseous environment by a vapor-phase hydrolysis of a silicon compound instead of by the usual aqueous precipitation process. Its outstanding properties are high chemical purity, low water content, enormous external surface area, and high degree of particle separation. Cab-o-sil functions in extremely small guantities as a reinforcing agent in rubber and plastics, a suspending and flatting agent in paints, as a thixotropic agent in various resins, as an emulsion stabilizer, and as a thickening and gelling agent.

The manner in which the above liquid is used as a bonding agent is as follows: A thin slurry is made using Liquid #2A and the opaque or undercoat porcelain. This is then painted onto the appliance in the areas which are to receive porcelain and the slurry is then fired. A specific ratio of powder/liquid is not required. The conditions which are necessary for success are that the slurry is paintable and, after painting, produces a general blocking out of the underlying metal color.

It is believed that the particular constituents have the following functions in the alloys of this invention:

Nickel — Major component chosen for its inherent resistance to corrosive attack.

Chromium — To enhance the corrosion resistance of the alloy and also as a solid solution strengthener.

Molybdenum — Enhances the corrosion resistance of the alloy and adjusts the coefficient of thermal expansion of the alloy.

Aluminum — Added as a deoxidizer and affects the coefficient of thermal expansion of the alloy.

Silicon — Added as a deoxidizer and also aids in obtaining fluidity for ease of casting.

Manganese — Acts as a safeguard against any possible sulfur contamination

Iron — Lowers the coefficient of thermal expansion and contributes to the metal to porcelain bond.

Lanthanum, strontium, zirconium — The function of these elements is to effect a porcelain to metal bond.

Tungsten — Lowers the thermal expansion characteristics and aids in the porcelain to metal bond.

Gallium — Improves the bonding characteristics and increases the fluidity of the alloy to facilitate casting.

These alloys were designed for use as an under-structure onto which porcelain is fused for making a fixed bridge type of dental restoration. General characteristics of these alloys are:

1. Ability to successfully melt and cast using either an oxy/acetylene torch or an induction type casting machine.
2. Precision dental castings can be achieved when cast into dental investments.
3. Matching coefficients of thermal expansion between the alloys and the porcelains which are currently being used.
4. Corrosion resistance to oral cavity fluids and tissue tolerance.
5. Brinell Hardness values in the range of 170–210.
6. Mechanical properties sufficient to withstand the forces employed in the mouth during mastication.

Aside from the practical evaluation of these alloys which involved the construction of porcelain fused to metal bridges, the following specific properties were determined in the manner described below.

Coefficient of Thermal Expansion

Equipment — Theta Dilatronic I, automatic recording dilatometer.

Test specimen — 2.000 inches long × 0.250 inches diameter

Test method — Determine the coefficient of thermal expansion between 200° and 1200° F.

Hardness

Equipment — Rockwell Hardness tester

Test specimen — case piece ½ × ¾ × ⅛ inches thick.

Test method — the hardness numbers were determined in three states:

1. As Cast Condition
2. Annealed — quenched after heating for 10 minutes at 1290° F.
3. Heat treated — 1800° F. for 30 minutes followed by a slow air cool.

Conversion to Brinell hardness via conversion chart for this type of alloy.

Tensile Properties

Equipment — Instron Tensile Machine

Test Specimen: cast piece 2⅞ inches long with 12024 threaded ends and a radius of ¼ inch from the threaded portion to the test area. The test area is 1⅜ inches long with a diameter of 0.09 ± 0.01 inch diameter.

NOTE: This is the specimen required by the ADA in Specification No. 14.

Corrosion and Tarnish Resistance

Adequate corrosion resistance was determined through a compilation of results of tests involving implant studies, in-vitro corrosion resistance vs. a negative control, and through clinical evaluations.

Tarnish resistance is evaluated by exposure to a dilute iodine-alcohol solution at 37° C.

The following properties were determined from the aforementioned tests:

A typical alloy gives the following results:

| As Cast Condition | |
|---|---|
| proportional Limit (psi) | 60,000 |
| 0.2 Yield Stress (psi) | 75,000 |
| Ultimate Tensile Strength (psi) | 85,000 |

-continued

| | |
|---|---|
| Elastic Modulus (psi) | 25-26 × $10^6$ |
| Elongation (%) | 2.15 |
| Hardness, Rockwell B | 93-99 |
| Heat Treated Condition | |
| Proportional Limit (psi) | 40,000 |
| 0.2% Yield Strength (psi) | 51,000 |
| Ultimate Tensile Strength (psi) | 75,000 |
| Elastic Modulus (psi) | 25-26 × $10^6$ |
| Elongation (%) | 6.6 |
| Hardness, Rockwell B | 85-91 |
| Thermal Expansion 8.25 × $10^{-6}$ in/in ° F. | |

Additional examples of this invention are as follows:

EXAMPLE IV

| Element | Preferred Composition | Composition Range |
|---|---|---|
| Nickel | 75.4 | Balance |
| Chromium | 13.5 | 10.0-15.0 |
| Molybdenum | 5.0 | 1.0-7.0 |
| Aluminum | 3.0 | 1.0-5.0 |
| Silicon | 1.0 | 0.5-2.0 |
| Magnanese | 0.1 | 0.01-0.2 |
| Tungsten | 1.5 | 0-5.0 |
| Strontium, Lanthanum and/or Zirconium individually or as a combination of Strontium and Zirconium | 0.5 | 0.2-2.0 |
| | 100.0% | |

EXAMPLE V

| Element | Preferred Composition | Composition Range |
|---|---|---|
| Nickel | 75.4 | Balance |
| Chromium | 13.5 | 10.0-15.0 |
| Molybdenum | 5.0 | 1.0-7.0 |
| Aluminum | 3.0 | 1.0-5.0 |
| Silicon | 1.0 | 0.5-2.0 |
| Manganese | 0.1 | 0.01-0.2 |
| Iron | 1.0 | 0-2.5 |
| Strontium, Lanthanum and/or Zirconium individually or as a combination of Stronium and Zirconium | 0.5 | 0.2-2.0 |
| Tungsten | 0.5 | 0-2.5 |
| | 100.0% | |

What is claimed is:

1. A nonprecious alloy consisting essentially of the following constituents in the indicated percentages by weight:

| Contituent | Proportional Range |
|---|---|
| Nickel | Balance |
| Chromium | 10.0-22.0 |
| Aluminum | 1.0-5.0 |
| Silicon | 0.5-2.0 |
| Manganese | 0.01-0.2 |
| Molybdenum | 0.0-7.0 |

and one of the following Groups A or B:

| | |
|---|---|
| Group A | |
| Strontium, lanthanum and/or zirconium individually or as a combination of strontium and zirconium, | 0.2-2.0 |
| either iron or tungsten seperately or in combination | 0.0-5.0 |
| Group B | |
| Strontium, lanthanum and/or zirconium individually or as a combination of strontium and zirconium, | 0.0-2.0 |
| gallium, | 1.0-3.0 |
| iron | 0.0-1.0. |

2. A nonprecious alloy consisting essentially of the following constituents in the indicated ranges of percentages by weight.

| Constituent | Proportional Range |
|---|---|
| Nickel | Balance |
| Chromium | 10.0-15.0 |
| Molybdenum | 1.0-7.0 |
| Aluminum | 1.0-5.0 |
| Silicon | 0.5-2.0 |
| Manganese | 0.01-0.2 |
| Iron | 0-5.0 |
| An element selected from the group consisting of Strontium, Lanthanum, Zirconium or a combination of Strontium and Zirconium | 0.2-2.0. |

3. A nonprecious alloy consisting essentially of the following constituents in the indicated percentages by weight:

| Constituent | Composition |
|---|---|
| Nickel | 25.4 |
| Chromium | 13.5 |
| Molybdenum | 5.0 |
| Aluminum | 3.0 |
| Silicon | 1.0 |
| Manganese | 0.1 |
| Iron | 1.5 |
| An element selected from the group consisting of Strontium, Lanthanum, Zirconium or a combination of Strontium and Zirconium | 0.5. |

4. A nonprecious alloy consisting essentially of the following constituents in the indicated percentages by weight:

| Constituent | Proportional Range |
|---|---|
| Nickel | Balance |
| Chromium | 10.0-15.0 |
| Molybdenum | 1.0-5.0 |
| Aluminum | 1.0-5.0 |
| Silicon | 0.5-2.0 |
| Manganese | 0.01-0.2 |
| An element selected from the group consisting of Strontium, Lanthanum, Zirconium or a combination of Strontium and Zirconium | 0.2-2.0 |
| Tungsten | 0.5-5.0. |

5. A nonprecious alloy consisting essentially of the following constituents in the indicated ranges of percentages by weight:

| Constituent | Composition |
|---|---|
| Nickel | 78.4 |
| Chromium | 13.5 |
| Molybdenum | 1.5 |
| Aluminum | 3.0 |
| Silicon | 1.0 |
| Manganese | 0.1 |
| An element selected from the group consisting of Strontium, Lanthanum, Zirconium or a combination of Strontium and Zirconium | 0.5 |
| Tungsten | 2.0. |

6. A nonprecious alloy consisting essentially of the following constituents in the indicated ranges of percentages by weight:

| Constituent | Proportional Range |
|---|---|
| Nickel | Balance |
| Chromium | 10.0-22.0 |
| Molybdenum | 0.0-3.0 |
| Aluminum | 1.0-5.0 |
| Silicon | 0.5-2.0 |
| Manganese | 0.01-0.2 |
| An element selected from the group consisting of Strontium Lanthanum, Zirconium or a combination of Strontium and Zirconium | 0.0-2.0 |
| Gallium | 1.0-3.0 |
| Iron | 0.0-1.0. |

7. A nonprecious alloy consisting essentially of the following constituents in the indicated ranges of percentages by weight:

| Constituent | Composition |
|---|---|
| Nickel | 78.1 |
| Chromium | 13.5 |
| Molybdenum | 1.5 |
| Aluminum | 3.0 |
| Silicon | 1.0 |
| Manganese | 0.1 |
| An element selected from the group consisting of Strontium, Lanthanum, Zirconium or a combination of Strontium and | 0.5 |
| Zirconium | 0.5 |
| Gallium | 2.0 |
| Iron | 0.3. |

8. A nonprecious alloy consisting essentially of the following constituents in the indicated ranges of percentages by weight.

| Constituent | Proportional Range |
|---|---|
| Nickel | Balance |
| Chromium | 10.0-15.0 |
| Molybdenum | 1.0-7.0 |
| Aluminum | 1.0-5.0 |
| Silicon | 0.5-2.0 |
| Manganese | 0.01-0.2 |

-continued

| Constituent | Proportional Range |
|---|---|
| Tungsten | 0-5.0 |
| An element selected from the group consisting of Strontium, Lanthanum, Zirconium or a combination of Strontium and Zirconium | 0.2-2.0. |

9. A nonprecious alloy consisting essentially of the following constituents in the indicated ranges of percentages by weight.

| Constituent | Proportional Range |
|---|---|
| Nickel | Balance |
| Chromium | 10.0-15.0 |
| Molybdenum | 1.0-7.0 |
| Aluminum | 1.0-5.0 |
| Silicon | 0.5-2.0 |
| Manganese | 0.01-0.2 |
| Iron | 0-2.5 |
| Tungsten | 0-2.5 |
| An element selected from the group consisting of Strontium, Lanthanum, Zirconium or a combination of Strontium and Zirconium | 0.2-2.0. |

10. A nonprecious alloy consisting essentially of the following constituents in the indicated percentages by weight:

| Constituent | Composition |
|---|---|
| Nickel | 75.4 |
| Chromium | 13.5 |
| Molybdenum | 5.0 |
| Aluminum | 3.0 |
| Silicon | 1.0 |
| Manganese | 0.1 |
| Iron | 1.0 |
| Tungsten | 0.5 |
| An element selected from the group consisting of Strontium, Lanthanum, Zirconium or a combination of Strontium and Zirconium | 0.5. |

* * * * *

UNITED STATES PATENT AND TRADEMARK OFFICE

CERTIFICATE OF CORRECTION

PATENT NO. : 4,053,308

DATED : October 11, 1977

INVENTOR(S) : John A. Tesk, et al

It is certified that error appears in the above-identified patent and that said Letters Patent are hereby corrected as shown below:

Column 5, line 22, Example IV, change "Magnanese" to -- Manganese --.

Column 5, line 47, Claim 1, change "Contituent" to -- Constituent --

Column 6, line 23, Claim 3, change "25.4" to -- 75.4 --

Column 7, line 29, Claim 7, delete the first occurrence of "0.5".

Signed and Sealed this

*Twenty-fifth* Day of *April 1978*

[SEAL]

*Attest:*

RUTH C. MASON
*Attesting Officer*

LUTRELLE F. PARKER
*Acting Commissioner of Patents and Trademarks*